(12) United States Patent
Chen et al.

(10) Patent No.: US 10,898,617 B2
(45) Date of Patent: Jan. 26, 2021

(54) MEDICAL PRODUCTS AND METHODS CONFIGURED FOR CONTROLLED RELEASE OF NITRIC OXIDE

(71) Applicant: BIOCREDE INC., Plymouth, MI (US)

(72) Inventors: Hao Chen, Ann Arbor, MI (US); Kevin Renehan, South Lyon, MI (US); Kwun Yin Ho, Ann Arbor, MI (US); Alexander Wolf, Ann Arbor, MI (US)

(73) Assignee: BIOCREDE INC., Monrovia, CA (US)

( * ) Notice: Subject to any disclaimer, the term of this patent is extended or adjusted under 35 U.S.C. 154(b) by 214 days.

(21) Appl. No.: 15/876,190

(22) Filed: Jan. 21, 2018

(65) Prior Publication Data
US 2018/0207323 A1 Jul. 26, 2018

Related U.S. Application Data

(60) Provisional application No. 62/448,960, filed on Jan. 21, 2017.

(51) Int. Cl.
| | | |
|---|---|---|
| *A61L 29/16* | (2006.01) | |
| *A61L 29/04* | (2006.01) | |
| *A61L 29/06* | (2006.01) | |
| *A61L 31/16* | (2006.01) | |
| *A61L 31/04* | (2006.01) | |
| *A61L 31/06* | (2006.01) | |
| *A61L 15/44* | (2006.01) | |
| *A61L 15/46* | (2006.01) | |
| *A61L 29/14* | (2006.01) | |
| *A61L 15/42* | (2006.01) | |
| *A61L 31/14* | (2006.01) | |
| *A61K 9/70* | (2006.01) | |

(52) U.S. Cl.
CPC ............ *A61L 29/16* (2013.01); *A61K 9/7084* (2013.01); *A61L 15/42* (2013.01); *A61L 15/44* (2013.01); *A61L 15/46* (2013.01); *A61L 29/041* (2013.01); *A61L 29/043* (2013.01); *A61L 29/06* (2013.01); *A61L 29/14* (2013.01); *A61L 31/042* (2013.01); *A61L 31/046* (2013.01); *A61L 31/06* (2013.01); *A61L 31/14* (2013.01); *A61L 31/16* (2013.01); *A61L 2300/114* (2013.01); *A61L 2300/404* (2013.01); *A61L 2300/42* (2013.01); *A61L 2400/18* (2013.01); *A61L 2420/02* (2013.01)

(58) Field of Classification Search
CPC .......... A61L 2300/404; A61L 2300/42; A61L 2400/18; A61L 2420/02; A61L 29/041; A61L 29/043; A61L 29/06; A61L 29/16; A61L 31/042; A61L 31/046; A61L 31/06; A61L 31/16
See application file for complete search history.

(56) References Cited

U.S. PATENT DOCUMENTS

| | | | |
|---|---|---|---|
| 5,187,305 A | 2/1993 | Thompson et al. | |
| 5,519,020 A | 5/1996 | Smith et al. | |
| 6,706,274 B2 | 3/2004 | Hermann et al. | |
| 6,747,062 B2 | 6/2004 | Murrell | |
| 7,750,201 B2 * | 7/2010 | Patel | A61F 13/00029 424/443 |
| 7,829,553 B2 | 11/2010 | Arnold et al. | |
| 8,992,945 B2 | 3/2015 | Lee et al. | |
| 9,566,372 B2 | 2/2017 | Handa et al. | |
| 2005/0107870 A1 * | 5/2005 | Wang | A61L 31/10 623/1.44 |
| 2006/0008529 A1 | 1/2006 | Meyerhoff et al. | |
| 2006/0039950 A1 | 2/2006 | Zhou et al. | |
| 2012/0136323 A1 * | 5/2012 | Stasko | A61L 15/225 604/290 |
| 2015/0366831 A1 | 12/2015 | Brisbois et al. | |
| 2017/0028106 A1 | 2/2017 | Brisbois et al. | |

FOREIGN PATENT DOCUMENTS

| | | |
|---|---|---|
| WO | WO0170199 | 9/2001 |
| WO | WO2003026717 A1 | 4/2003 |
| WO | WO2007012165 A1 | 2/2007 |
| WO | WO2009131931 A1 | 10/2009 |

OTHER PUBLICATIONS

Yaqi Wo et al., Origin of Long-Term Storage Stability and Nitric Oxide Release Behavior of CarboSil Polymer Doped with s-Nitroso-N-acetyl-D-penicillamine, ACS Appl. Mater. Interfaces, Sep. 22, 2015, pp. 22218-22227, vol. 7.
Alessandro Colletta et al., S-Nitroso-N-acetylpenicillamine (SNAP) Impregnated Silicone Foley Catheters: A Potential Biomaterial/Device to Prevent Catheter-Associated Urinary Tract Infections, ACS Biomater. Sci. Eng. Apr. 27, 2015, pp. 416-424, vol. 1.
Elizabeth Brisbois et al., Improved Hemocompatibility of Multilumen Catheters via Nitric Oxide (NO) Release from S-Nitroso-N-acetylpenicillamine (SNAP) Composite Filled Lumen, ACS Appl. Mater. Interfaces, Oct. 13, 2016, pp. 29270-29279, vol. 8.
Hitesh Handa et al., In vitro and in vivo study of sustained nitric oxide release coating using diazeniumdiolate-oped poly(vinyl chloride) matrix with poly(lactide-co-glycolide) additive, J Mater Chem B Mater Biol Med. Aug. 7, 2013; 1(29): 3578-3587.

(Continued)

*Primary Examiner* — Anna R Falkowitz
(74) *Attorney, Agent, or Firm* — Coastal Patent Law Group, P.C.

(57) ABSTRACT

The disclosure concerns various medical devices implemented to provide a nitric oxide rich environment for anti-microbial or anti-thrombogenic benefits. The medical device generally includes a nitric oxide donor material that is contained within a sealed cavity, and a transport medium that defines and captivates the entirety of the cavity, wherein the transport medium is permeable to both water and nitric oxide. As the nitric oxide donor material becomes saturated with water from the surrounding tissue or fluids, nitric oxide is chemically released, and the resulting nitric oxide is communicated through the transport medium to a treatment site for anti-microbial and anti-thrombogenic benefits.

18 Claims, 7 Drawing Sheets

(56) References Cited

OTHER PUBLICATIONS

Harvey Liu et al., Novel Delivery System for the Bioregulatory Agent Nitric Oxide, Chem. Mater. 2009, 21, 5032-5041.
Antibacterial textile fibre material and method of obtaining it (WIPO cited reference, D3).
W.L.Robb, Thin Silicone Membranes—Their Permeation Properties and Some Applications, Annals New York Academy of Sciences (WIPO cited reference, D4).
Jun Yang, Potential Anti-Thrombotic Nitric Oxide Generating Layer-by-Layer Assembly, University of Michigan, 2010 (WIPO cited reference, D5).
Marcus J. Goudie et al., Characterization of an S-nitroso-N-acetylpenicillamine-based nitric oxide releasing polymer from a translational perspective, Int J Polym Mater. 2016 ; 65(15): 769-778.

* cited by examiner

MEDICAL PRODUCTS AND METHODS CONFIGURED FOR CONTROLLED RELEASE OF NITRIC OXIDE

GOVERNMENT LICENSE RIGHTS

This invention was made with government support under 1R41DK100161; 1R41DK101206; 1R43DK102189; 2R42DK100161; 5R42DK100161; 1R43GM119883; and 2R44GM119883 each awarded by the National Institute of Health (NIH). The government has certain rights in the invention.

TECHNICAL FIELD

This invention relates to medical device products and methods for making and using the same.

More particularly, the invention is directed to medical devices configured to receive moisture through a transport medium, and upon receiving the moisture, providing a sustained and controlled release of nitric oxide and other beneficial compounds for anti-microbial and anti-thrombogenic treatment at a targeted site.

BACKGROUND ART

Nitric oxide (NO) has been demonstrated to possess several key physiological functions including vasodilation, anti-platelet activity, and anti-microbial/anti-viral potency. It serves a critical role as signaling molecule and is produced endogenously in localized concentrations by nearly every type of tissue, including endothelial cells, neural cells, and macrophages. Medical research continues to unveil an expanding range of therapeutic applications for NO, and materials research has focused toward developing and implementing NO release for surfaces prone to blood contact or that make up implanted devices to control infection, minimize biofilm formation, and reduce inflammation at sites of interface with the body. Exogenous NO given as inhalation therapy has demonstrated a short half-life and insolubility in physiological fluids. Systemic exogenous delivery was achieved through administration of organic nitrite precursors (e.g. nitroglycerine tablets, ointments, intravenous suspensions, and transdermal wound dressings). While the human body rapidly converts nitroglycerin into NO, enzyme and co-factor pathways required to activate these nitrate compounds are rapidly exhausted, resulting in drug tolerance complications. Furthermore, maintaining systemic NO delivery can result in serious physiological complications such as hypotension and free radical cell damage. Therefore, localized or site-specific NO delivery has been the subject of intense focus and research.

Although NO is a stable radical, it rapidly reacts with hemoglobin and oxygen, complicating delivery to the site of interest. The antimicrobial activity of NO includes bacterial killing and preventing surface biofilm formation. Bacterial infections and biofilm formation are common complications with modern biomedical devices, especially those implanted within the patient. Bacteria possess a unique ability to fabricate biofilms on surfaces where the organism secretes a polysaccharide matrix to house the colonies. This matrix provides serves two purposes: to supply nutrients to sustain growth in harsh environments and shield the bacteria against the host foreign body defense mechanisms and antibiotics. Biofilms can act as a source of chronic infection, thereby prolonging patient recovery time. Among its many physiological roles, NO functions as an antimicrobial agent and as an accelerant to the wound healing process. NO possesses a broad-spectrum of antibacterial activity, demonstrating high killing potency of both gram-positive and gram-negative bacterial strains. Lower levels of localized NO release are also reported to efficiently disperse biofilms that have formed on the surface of indwelling medical devices through bacterial signaling pathways. The NO flux from endothelial cells has been estimated by Vaughn, et al, Am. J. Physiol., Vol. 274 (Heart Cir. Physiol., Vol. 43) page H2163 (1998) to be $4.1 \times 10^{-10}$ mol $cm^{-2}$ $min^{-1}$ and experimental data from published by Radomski, et al. S. Proc. Natl. Acad. Sci. USA, Vol. 87, page 5193 (1990) which estimated NO flux for stimulated endothelial cells to be $1.6 \times 10^{-10}$ mol $cm^{-2}$ $min^{-1}$ and approximately $0.50 \times 10^{-10}$ mol $cm^{-2}$ $min^{-1}$ for unstimulated control cells. Similar surface fluxes produced by NO donor containing surfaces is therapeutically relevant and capable of achieving bacterial killing based on findings from Wo, et al. ACS Appl. Mater. Interfaces, Vol. 7, 22218-22227 (2015).

Bacterial cells organize themselves and produce expolysaccharides to become an almost irreversible system. Later, as mushroom-shape surfaces start to form, groups of bacterial cells detach and colonize new surfaces. The commonly encountered mineral encrustation is hydrolyzed by urease producing bacteria, leading to both catheter associated infections and catheter clog, requiring surgical removal. In developing countries, bacterial resistance is 3 to 5 times higher than international standards, leading to increased lengths of stay from 10-15 days dependent on the surgery, added medical costs, and a two-fold increase in mortality. Further, Hospital acquired infections (HAI) leading to sepsis and septic shock are the leading cause of patient mortality and high medical costs, and 30% of the 18 million patients globally contracting HAI leading to sepsis die at the intensive care units annually, including 200,000 of those 750,000 patients who die in the US. Elderly and young/adult immune-compromised patients are particularly at risk for sepsis-induced infections, with more than 50% of severe sepsis cases occurring in patients of 65 years and older. Infections are usually attributed to the long-term use of indwelling catheters as described below.

Catheter associated urinary tract infections (CAUTI) contribute to almost 800 thousand nosocomial hospital infections annually with a cumulative incidence of 3-6% per day of catheterization (50% at 10 days, >90% at 28 days, 100% long term) leading to complications such as cystitis, pyelonephritis, gram-negative bacteremia, prostatitis, epididymitis, urosepsis, septicemia, etc., in patients. Further, secondary nosocomial bloodstream infections can occur and lead to an associated mortality rates of nearly 10%. Further, tunneled dialysis catheters often lead to deep-seated infections such as infective endocarditis, osteomyelitis and epidural abscesses. Approximately 90,000 patients are annually admitted to hospitals for dialysis catheter related bacteremia or sepsis, and each central line-associated bloodstream nosocomial infection normally adds an average of $47,000 to the cost of care and 14.6 days to the length of stay.

Various active agents have been coated onto the surface of these medical devices for antimicrobial activity such as an antimicrobial metal or an organic antimicrobial agent. There are a vast amount of silver and silver salt coated medical devices (U.S. Pat. Nos. 5,395,651; 5,747,178; 5,320,908, 4,054,139; 4,581,028; and others); however, these coating applications are hard to control and to retain, and thus producing and maintaining sustained dosing remains a challenge. Other anti-bacterial surfaces use organic antimicrobial agents such as chlorhexidine and its derivatives (U.S.

Pat. Nos. 4,999,210; 5,013,306; and 5,707,366); however, these increase bacterial resistance. Another group uses aluminosilicates or zeolites with exchange ions from a metal (U.S. Pat. Nos. 4,2525,410; 4,775,585; 4,911,898; 4,911,899; 5,064,599; 4,938,955; 5,556,699), but suffer from similar biofilm formation rates when compared to control.

Additionally, medical devices made of polymer matrices such as polyethylene glycol, poly(vinyl alcohol), and poly(vinyl-pyrrolidone) have been doped with S-nitrosothiols (RSNOs) for potential medical applications to have antibacterial properties; however, these have high RSNO leaching and NO release is limited to only a few hours. When RSNOs are covalently bound to fumed silica particles in polyurethanes, polyesters, silicone elastomers, self-assembled monolayers, xerogels, or poly(vinyl methyl ether-co-maleic anhydride) (U.S. Pat. Pub, 2009/0118819), medical device surfaces crack or pit, leading to high inflammations and low shelf life. Furthermore, antimicrobial coatings composed from gentian violet and chlorhexidine (U.S. Pat. Pub. 2014/0302113) must be kept in a solution containing equivalent or greater concentrations of the same drug from initial preparation to maintain viability until use, thereby leading to shelf life limitations. In general, surface modifications, surface coatings, and doping also may adversely affect other important device properties, such as the smoothness of the surface. In many cases, the surface becomes less smooth post-treatment, inhibiting the ability to slide the device along or into tissue. Surface treatments that enhance lubricity without compromising structural integrity, release properties, or intended function are highly desirable.

Next, NO delivery using nitrate prodrugs such as nitroglycerin tablets, intravenous suspensions, sprays, and transdermal patches require body enzymes and co-factors to activate NO release and deplete rapidly, thereby resulting in drug tolerance with devastating side effects. Many prodrug based treatments yield a systemic effect in the body, rather than localized NO delivery at a site of infection or the implanted device.

In summary, bacterial infections remain a significant risk and cost associated with many medical devices that contact patient tissue, particularly those with extended contact over multiple days, such as implanted devices and catheters. Accordingly, there is a critical need for medical devices with improved material durability and antimicrobial effectiveness, while retaining other advantageous properties of current devices, such as slick/low friction surfaces and manufacturability. Long-term indwelling, implanted, or transdermal medical devices are particularly susceptible to complications from bacterial infections and may benefit from long-term sustained bactericidal effectiveness.

SUMMARY OF INVENTION

Technical Problem

Conventional medical devices, such as catheters and pads, inter alia, remain subject to a myriad of problems connected to bacterial proliferation, infection, and thrombogenesis. These problems can be mitigated with treatments that implement a localized nitric oxide rich environment; however, novel products and methods are needed which efficiently deliver and sustain a useful dose of nitric oxide over a treatment duration. The conventional products and methods which attempt to implement such a sustained nitric oxide rich environment for anti-microbial and anti-thrombogenic purposes have remained inadequate and presently continue to fail in achieving a therapeutically acceptable standard.

Solution to Problem

Generally, we propose the implementation of a nitric oxide donor material that is contained within a sealed cavity, and a transport medium that defines and captivates the entirety of the cavity, wherein the transport medium is permeable to both water and nitric oxide. As the nitric oxide donor material becomes saturated with water from the surrounding tissue or fluids, nitric oxide is chemically released, and the resulting nitric oxide is communicated through the transport medium to a treatment site for anti-microbial and anti-thrombogenic benefits.

This implementation, which we may refer to herein as a "passive nitric oxide transport technique (PNOTT)" or simply "technique", can be similarly applied to a broad variety of medical devices, including but not limited to: a transdermal patch, catheter, implantable device, implantable pouch, implantable patch, anastomosis ring, woven material, diabetic foot ulcer wound dressing, chronic wound dressing, burn wound dressing, trauma wound dressing, mouth ulcer pad, negative pressure wound dressing accessory, wipe, swab stick, gauze accessory, condom, acne pad, acne wipe, facial mask, or a sock.

Exemplary nitric oxide donor materials for use with the invention may comprise: diazeniumdiolated diamine, S-nitroso-albumin, S-nitroso-N-acetyl-DL-penicillamine (SNAP), S-nitrosoglutathione (GSNO), diazeniumdiolated dibutylhexyldiamine (DBHD N2O2), S-nistrosocystine, Diethylenetriamine/nitric oxide adduct (DETA/NO), Diethylamine NONOate (DEA/NO), Dipropylenetriamine NONOate (DPTA/NO), 6-(2-Hydroxy-1-methyl-2-nitrosohydrazino)-N-methyl-1-hexanamine (MAHMA/NO), 1,2,4-triazole analogues of diclofenac, NCX 4040, ketoprofen-NO hybrids, nitrosoproline (PROLI/NO), spermine (SPER/NO), S-nitroso-N-acetyl-DL-penicillamine (SNAP), S-nitroso-N-acetylcysteine, nitroglycerin (GTN), isorbide dinitrate (ISDN) or a derivative or combination thereof.

For purposes herein, the term "transport medium" is defined as a physical medium substantially surrounding a cavity portion of a medical device product. The transport medium may comprise a coating substantially surrounding a particle, fiber, woven material, or pad. Alternatively, the transport medium may comprise a lumen. The term "transport medium" as-used herein is intended to broadly encompass any physical medium which is configured to define and captivate a cavity for containing a nitric oxide donor material. Any openings disposed about the transport medium may be sealed by conventional means to fully captivate the nitric oxide material.

The transport medium preferably comprises a biocompatible material, and more preferably a biocompatible polymer material. In this regard, the transport medium may comprise: cellulose, collagen, citrulline, arginine, tetrahydrobiopterin, ornithine, Nitric Oxide Synthase Trafficking Inducer (NOSTRIN), arigininosuccinate, L-citrulline malate, polyglucose, polyacrylonitrile, polykeratin, siloxane, carboxymethyl cellulose, polyester, polyurethane, polyfibrin, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, or derivatives and combinations thereof.

Permeability of the transport medium is a key component for successful practice of the invention. For example, a transport medium that has excessive permeability will likely communicate too much water into the cavity, or communicate water too quickly, and/or may release too much nitric oxide thereby exhausting the source and limiting the duration of therapeutic effectiveness; whereas a transport medium that has insufficient permeability may not communicate enough moisture into the cavity required to produce the desired level of nitric oxide from the donor material, and/or may inhibit transfer of nitric oxide through the transport medium to the delivery site. Permeability will be largely dependent on the type of device and the particular application; however, will be generally in the range of 40 to 55000 Barrers. One having skill in the art will recognize standard conventional methods for modulating permeability of the transport medium, such as selecting from available materials based on permeability factors, cross-linking, among other things, to achieve the desired level of passive nitric oxide transport through the transport medium.

While the desired level of nitric oxide delivered to the treatment site will be dependent on the type of device and the specific application, the desired level of nitric oxide will be generally on the order of 0.1-8.0 Flux Units, wherein a NO Flux Unit (nitric oxide) is defined as $1.0\times10^{-10}$ mol $cm^{-2}$ $min^{-1}$.

Advantageous Effects of Invention

By embedding a nitric oxide donor material within a medical device product, and surrounding the nitric oxide donor material with a selectively permeable transport medium for promoting passive nitric oxide transport in a controlled and sustained manner, the invention achieves an improvement over conventional medical devices, namely, the ability to provide a sustained nitric oxide rich environment at a treatment site adjacent to the medical device, for a duration for which the device is intended for use, thereby achieving anti-microbial and anti-thrombogenic goals and improving care.

DESCRIPTION OF EMBODIMENTS

In the following description, for purposes of explanation and not limitation, details and descriptions are set forth in order to provide a thorough understanding of various embodiments of the invention. However, it will be apparent to one skilled in the art that the invention may be practiced in other embodiments, including certain variations or alternative combinations that depart from these details and descriptions. As such, this disclosure is not intended to be limiting with respect to the spirit and scope of the invention as-claimed.

Example 1—Catheter

Turning now to the drawings, and in accordance with a first embodiment, an improved catheter being configured for anti-microbial and anti-thrombogenic treatment is disclosed.

Figure 1:
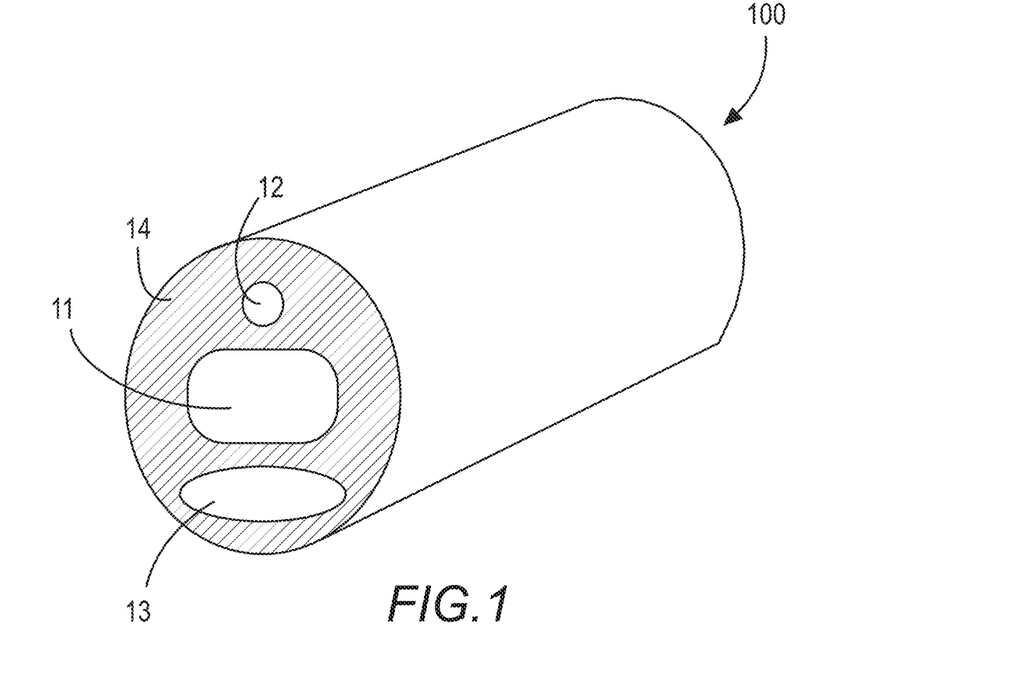
FIG. 1 shows a portion of a medical device having multiple lumens.

FIG. 1 shows a cross-section of a water-permeable tubular medical device 100, such as, for example, a tubular portion of a Foley urinary catheter, with at least a first lumen 11, a second lumen 12, and a third lumen 13. Each of the first thru third lumens are disposed within a water-permeable transport medium 14. The first lumen is sealed at the terminal ends (See FIG. 3) to define an enclosed reservoir or "cavity". Accordingly, as it relates to this illustrated embodiment, the first lumen 11 may also be referred to as a "cavity 11".

Figure 2:
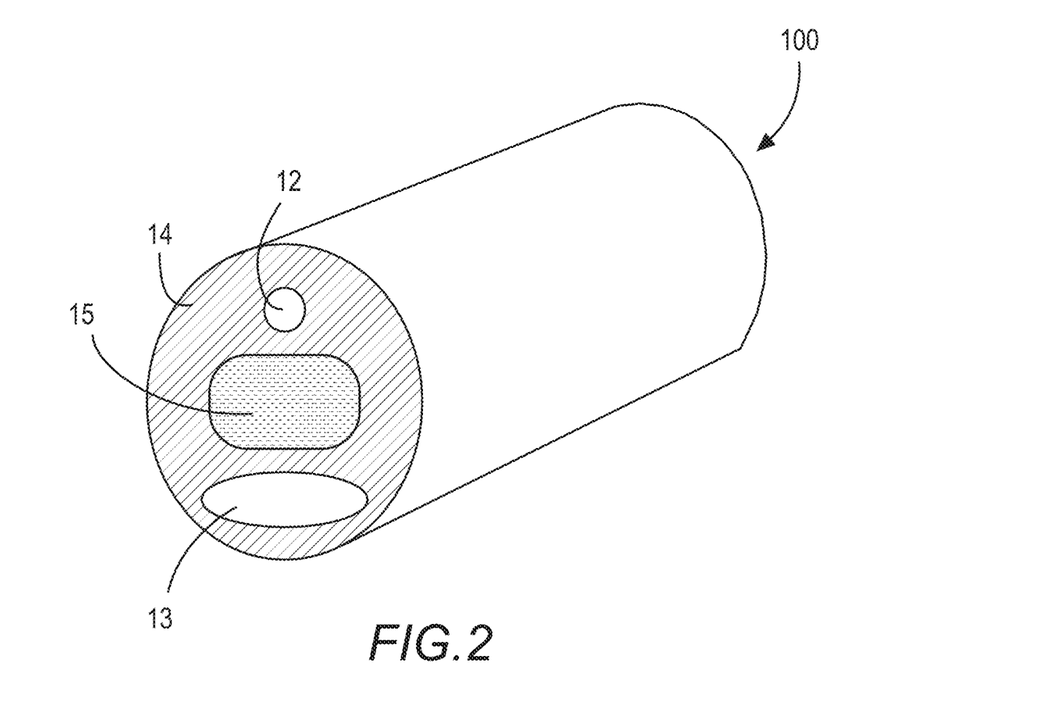
FIG. 2 shows the portion of the medical device of FIG. 1 having one lumen thereof filled with a nitric oxide donor material.

FIG. 2 shows the medical device 100 of FIG. 1 with the addition of a nitric oxide donor material 15 contained within the cavity 11. Here, the cavity 11 is a lumen-type cavity ("first lumen") extending along a length of the catheter; however, one with skill in the art will appreciate that any number, shape or design of the cavity may be implemented to yield one or more cavities which perform the same function in substantially the same manner. For example, in some other embodiments, multiple reservoirs or cavities may extend along a length of the catheter. However, in this example, surrounding the lumen-type cavity 11 is a transport medium 14. The transport medium substantially surrounds the cavity 11 and the nitric oxide donor material 15 therein.

Moisture from an adjacent environment or "treatment site" is permitted to permeate through the transport medium and into the cavity, wherein upon encountering the nitric oxide donor material a chemical reaction occurs thereby releasing nitric oxide from the nitric oxide donor material. The nitric oxide within the cavity is then capable of permeating through the transport medium into the adjacent environment where it functions as an anti-microbial and anti-thrombogenic agent at the treatment site.

In addition to the cavity 11, nitric oxide donor material 15, and transport medium 14, the medical device 100 (a catheter in this example) comprises a second lumen 12. The second lumen 12 may provide an additional cavity for housing a nitric oxide donor material, or may have some ancillary function, such as a port for balloon inflation.

Moreover, the medical device 100 may comprise a third lumen 13. The third lumen may provide an additional cavity for housing a nitric oxide donor material, or may have some ancillary function, such as to guide the flow and transport of body fluids, for example urine.

Figure 3:
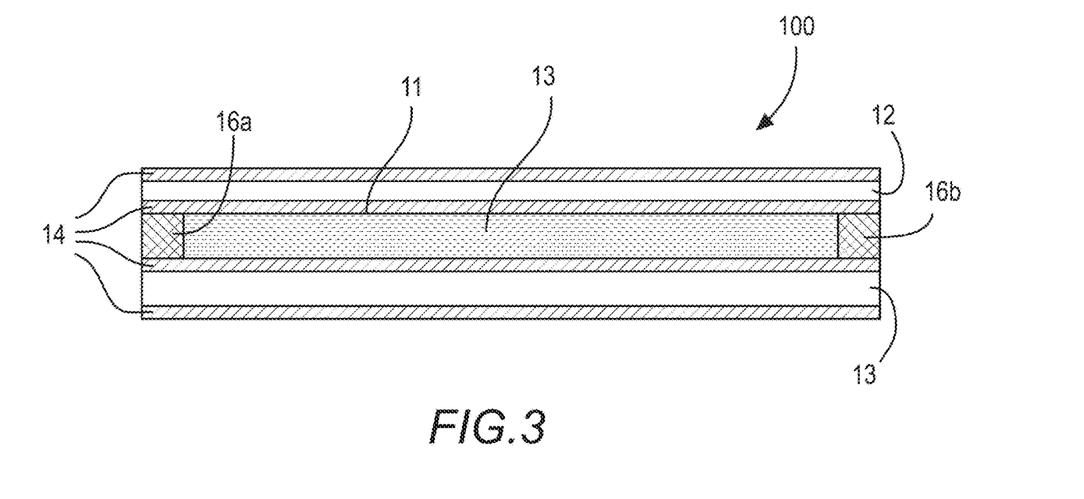
FIG. 3 shows a side view of the medical device of FIGS. 1-2, wherein the lumen filled with a nitric oxide donor material comprises plugs on either end to seal a cavity within the device.

Accordingly, the medical device may comprise one or more lumens, and each of the lumens may be independently configured to comprise a nitric oxide donor material therein.

Where the cavity forms a lumen, the openings at either end of the lumen may be sealed as shown in FIG. 3. This can be accomplished by inserting plugs 16a; 16b at either exposed end, or by any conventional means that would be appreciated by one having skill in the art. The result would be a contained cavity 11 with the nitric oxide donor material 15 therein. Here, the catheter comprises a first lumen that is sealed to form the cavity 11 therein, a second lumen 12 and third lumen 13. The first lumen is filled with a nitric oxide donor material 13 and sealed at the openings.

Third lumen 15 is typically larger than 2 mm$^2$, but depends on the size of medical device 100, which is typically measured in French (Fr). The first thru third lumens may comprise any functionally appropriate shape, including annular, such as a circular or oval shape. Although not depicted, in certain approaches the device contains only one or two lumens, with at least a first lumen containing a nitric oxide donor material 15. Additionally, or alternatively, the device may comprise more than three lumens, with at least a first lumen forming a cavity containing a nitric oxide donor material 13.

In one embodiment, the nitric oxide donor material may comprise a mixture of nitric oxide donor materials. In certain aspects, the mixture comprises a powdered form of the nitric oxide donor material 13. Additionally, or alternatively, the mixture may comprise excipients that modify or modulate the properties of the nitric oxide donor material 13 and the performance of the medical device 100. These properties may include, but are not limited to: shelf life, stability, release rate, and potency.

Figure 4:
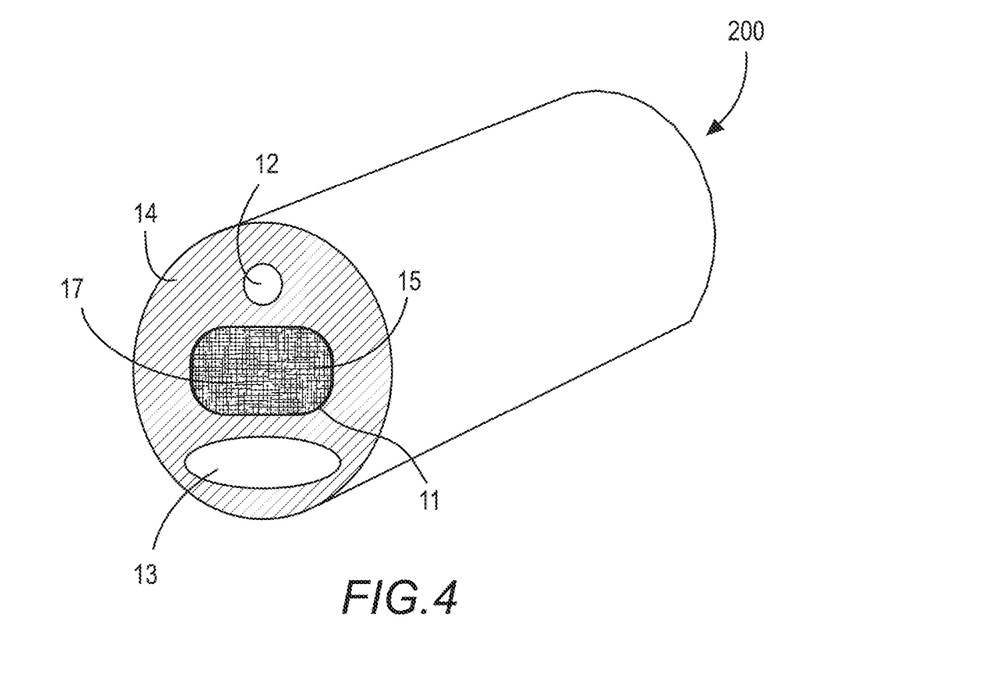
FIG. 4 shows a portion of a medical device wherein a holding material is captured within a lumen, the holding material including a nitric oxide donor material embedded therein.

In another embodiment, is illustrated FIG. 4, the nitric oxide donor material can be embedded in a holding material 17. For example, holding material 17 may comprise a woven material that serves as a matrix loosely holding the nitric oxide donor material 15. In certain embodiments, the holding material 17 may also include excipients to modify the properties of the nitric oxide donor material 15. The woven material or matrix can be a filament, or series of wound filaments. The nitric oxide donor material may be dissolved in a solvent, and saturated into the holding material prior to evaporation of the solvent. In this regard, the nitric oxide donor material can be embedded within the woven material along with any additional agents, excipients and the like.

FIG. 4 shows a medical device 200, wherein the nitric oxide donor material 15 is embedded in the holding material 17, and the holding material is further contained in the cavity 11 and surrounded by a transport medium 14. The medical device 200 also comprises a second lumen 12 and a third lumen 13.

In certain aspects, transport medium 14 comprises a material that is water permeable or semipermeable, thereby giving medical device 100; 200 water permeable properties such that water may permeate into one or more of the first thru third lumens, or the cavity containing nitric oxide donor material 15. In practice, transport medium 14 has a permeability coefficient of moisture that ranges from between approximately 40 to approximately 55000 Barrers, although any appropriate coefficient may be used to give appropriate device characteristics for the release of nitric oxide or other therapeutic molecules as described herein. In certain embodiments, transport medium 14 has a first permeability to water molecules in the gas phase and second permeability to water molecules in the liquid phase.

Additionally, or alternatively, transport medium 14 may comprise a material permeable or semipermeable to nitric oxide. For example, nitric oxide donor material 15 releases nitric oxide when the nitric oxide containing cavity (e.g., first lumen 11) is moist and the released nitric oxide permeates through transport medium 14. In certain embodiments, the released nitric oxide permeates through an inner surface of the first lumen through transport medium 14 and through an outer surface of the transport medium at a rate that is equivalent to or greater than that of localized endothelial cells, or 0.4-1.6 NO Flux Units, wherein a NO Flux Unit is defined as $1.0 \times 10^{-10}$ mol cm$^{-2}$ min$^{-1}$. In certain approaches, nitric oxide donor material 15 releases nitric oxide under physiological conditions in predictable quantities in the range of 0.4 to 4.0 NO Flux units for the duration of use.

In general, transport medium 14 may comprise a biocompatible material. In certain embodiments, the transport medium may be formed from a hydrophilic material. The transport medium may be formed from a polymer from the group consisting of: an α-acetal moiety, a β-acetal moiety, a hydroxyl moiety, a nitrile moiety, a nitrate ester moiety, and a carboxyl moiety. In certain approaches, the transport medium is formed from the group consisting of: cellulose (cotton, flax, hemp), polyglucose, polyacrylonitrile, polykeratin, polydimethylsiloxane, silicone, polyester, polyurethane, polyfibrin (silk), and mixtures thereof.

The medical device described in FIGS. 1-4 generally comprises a transport medium made of water-permeable materials such as cellulose (cotton, flax, hemp), fabric, polyglucose, polyacrylonitrile, polykeratin, polydimethylsiloxane, polyester, polyurethane, polyfibrin (silk), poly-paraphenylene terephthalamide (Kevlar), and mixtures thereof. These materials may form part of a medical device construct such as: catheters, implants, feeding tubes, arteriovenous catheters, balloon catheters, sutures, anastomosis rings, resuscitators, drainage tubes, nasal catheters, gastrostomy catheters, and oxygenators. This medical device construct form factor and design allows the release of nitric oxide after patient catheterization to provide antibacterial, anti-thrombosis, anti-stenosis, and antifungal properties to improve healing and prevent catheter dysfunction.

Example 2—Pad

Figure 5:
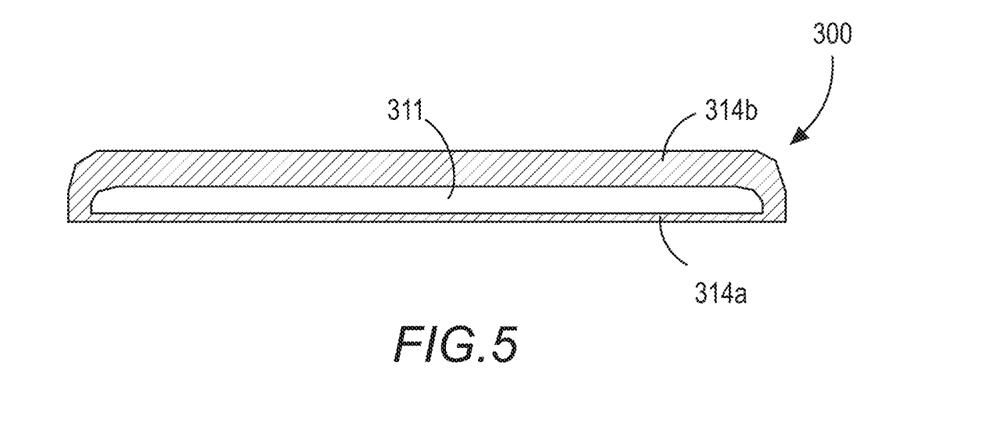
FIG. 5 shows a medical device pad having a cavity portion.
Figure 6:
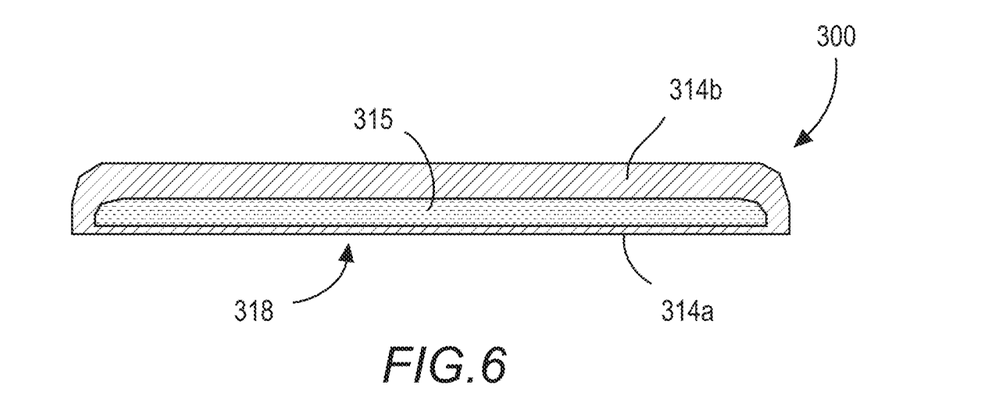
FIG. 6 shows the pad of FIG. 5 wherein the cavity portion contains a powdered nitric oxide donor material.
Figure 7:
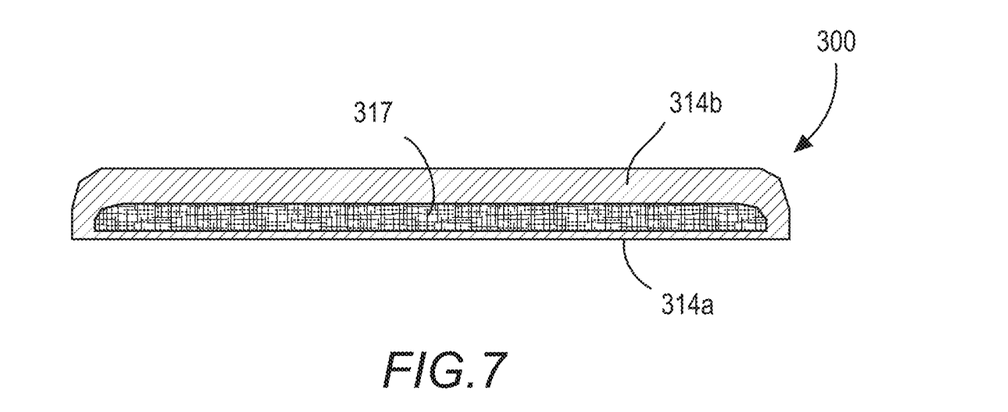
FIG. 7 shows a pad of FIG. 5 wherein the cavity portion contains a holding material and the holding material contains a nitric oxide donor material embedded therein.

In another embodiment, as illustrated in FIGS. 5-7, a medical device may take the form of a pad 300. The pad generally includes a transport medium 314 forming an enclosure around an inner cavity 311, wherein the inner cavity is filled with or otherwise comprises a nitric oxide donor material 315. Properties such as composition and thickness of the transport medium are selectively implemented to allow for permeability of water (moisture) into the cavity and nitric oxide out of the cavity.

The pad may comprise a flat contour 318 at the delivery side, or other contour for engaging an anatomical feature of a patient. The pad may be implemented as a medical dressing, wound healing pad, bandage, or other pad device as conventionally provided in the art.

Additionally, a thickness of the transport medium at the delivery side of the pad can have a second thickness 314b that is less than a first thickness 314a associated with the rest of the pad.

Figure 8:
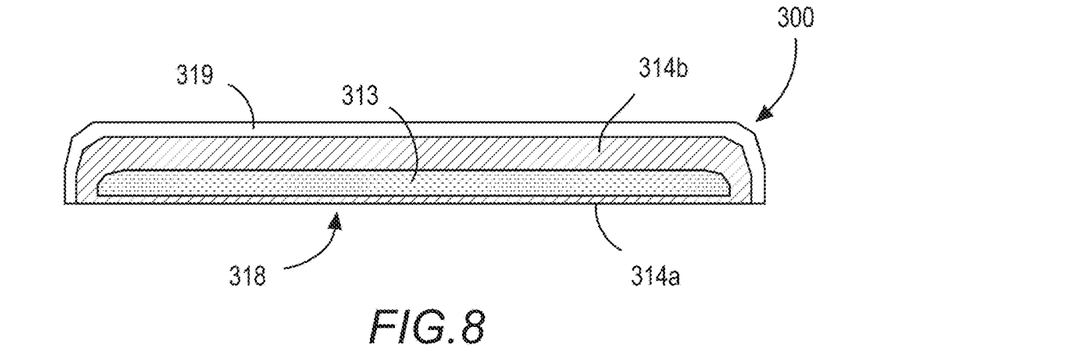
FIG. 8 illustrates a medical device pad having a coating on an outer layer.

As shown in FIG. 8, a coating 319 or additional layer can be applied to all sides of the pad except the delivery side such that the pad will have a higher permeability at the delivery side, thereby allowing a bulk of the nitric oxide to permeate through the delivery side of the pad.

In another embodiment, as illustrated in FIG. 6, the pad may comprise a first shell portion, and a second delivery portion, wherein the transport medium forms the delivery portion and wherein the shell portion is less permeable or non-permeable to water and/or nitric oxide. In this regard, the shell and transport medium combine to surround and encapsulate a cavity, wherein a nitric oxide donor material is contained within the cavity.

The pad 300 may be practiced with the nitric oxide donor material in a powdered form or mixture (FIG. 6). Again, as above, the powdered form may comprise a nitric oxide donor material, a mixture of nitric oxide donor materials, or a mixture of one or more nitric oxide donor materials, excipients and/or other active wound healing agents.

Alternatively, the pad 300 may be practiced with the nitric oxide donor material being embedded in a holding material.

The transport medium made of water-permeable materials such as cellulose (cotton, flax, hemp), fabric, polyglucose, polyacrylonitrile, polykeratin, polydimethylsiloxane, polyester, polyurethane, polyfibrin (silk), poly-para-phenylene terephthalamide (Kevlar), and mixtures thereof, is used in the creation of a biocompatible medical dressing.

The pad 300 can be used to cover and protect wounds sites as a bactericidal transdermal patch with breathability properties and enhance wound healing such as wound covers, catheter bandages, bandages, acne sites, and surgery wounds. The embodiments that are used in the creation of these biocompatible medical constructs may include ulcer pads, foot pads, sanitary pads, socks, condoms, diapers, tampons, socks, and wound covers.

Example 3—Multi-Phase Pad

In another embodiment, a multi-phase pad is disclosed. The multi-phase pad is configured to support wound healing by providing different agents and factors over time.

Figure 9:
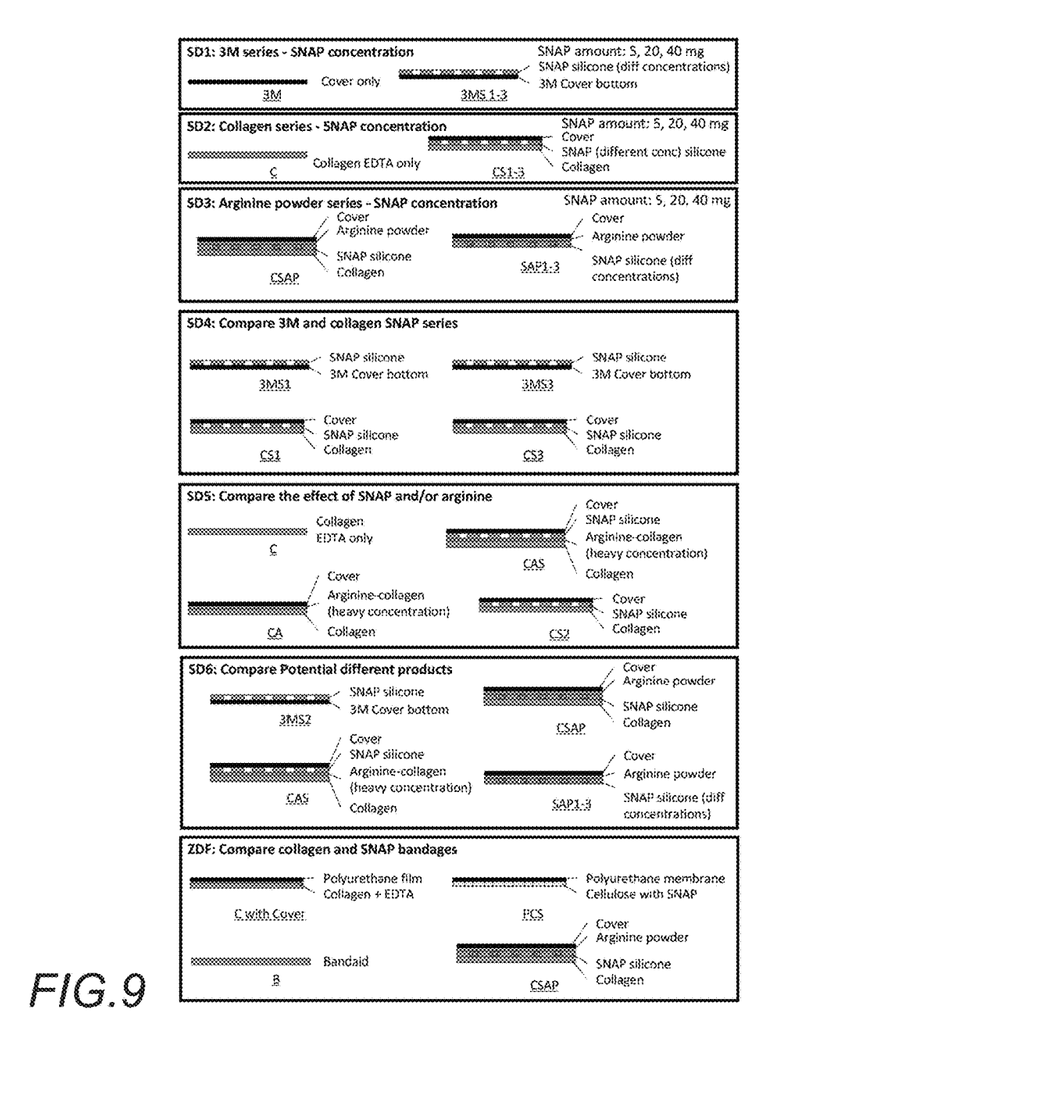
FIG. 9 shows various layered pads each configured with a combination of a nitric oxide donor material, EDTA, arginine, and/or collagen.

In an experiment, different dressing formulations containing a variety of ratios of SNAP, silicone, and optionally collagen (Type IV) were evaluated for NO flux over a 5-7 day interval. NO released from sample bandages was assessed via chemiluminescence at body temperatures (37.5° C.) in 10 mM PBS (pH 7.4, containing 100 μM EDTA) using the Nitric Oxide Analyzer (NOA) 280i (Boulder, Colo., USA) that measures NO release by placing the samples in a clear glass sample vessel elevated above a shallow reservoir of PBS buffered solution purged with a nitrogen gas bubble solution. In the cell vacuum, water vapor should contact the bandage solution without need. This setup was employed to simulate water vapor emanating from the dermal or wound surface. Samples reach a plateau nitric oxide release value within the sample vessel (in PPB or PPM), which is recorded converted into a NO flux value with the surface area of dressings. NO release from surfaces and devices, such as the catheters allow them to mimic the functions of endothelial cells lining the inner walls of all blood vessels, which endogenously release NO at localized fluxes of $(0.5-4.0)\times 10^{-10}$ mol cm$^{-2}$ min$^{-1}$. The NO Flux profiles from the sample bandages measured over a 5-7 day period are shown in FIG. 9. Nearly every SNAP/Silicone formulation dressing is characterized by an initially high burst of NO release on Day 1, which plateaus to 1.25 to $0.50\times 10^{-10}$ mol cm$^{-2}$ min$^{-1}$ (NO flux units) at the end of the study. Initially elevated NO flux values are important for rapid or accelerated initiation of the inflammation of the wound healing cascade and differentiation of macrophages from M1 to M2 phenotype. As wound healing progresses, localized nitric oxide concentrations should subside, and this behavior is displayed by the NO flux profiles of the sample bandages.

Zucker Diabetic Fatty (ZDF) rats (n=3) were used at 70 days age. Based on a 24-month lab-rat and 80-year human lifespans, these ZDF rats were roughly equivalent to 23-40-year-old human clinical research subjects. These animals have an inbred genetic lineage with a diabetic marker of predisposition for consistent development of Type 2 diabetes. ZDF rats can express a non-diabetic phenotype if kept on a normal diet or can be induced with Type 2 diabetes when fed a specific nutritional composition, namely Purina 5008 pellets after acclimation. The animals were initially non-diabetic and had an average weight of 312±15 g were housed in Biocrede animal facilities according to IACUC-approved husbandry protocols for feeding, cage cleaning, and enrichment. With increased age, ZDF rats are expected to have slightly slower progression of wound healing compared to younger animals, due to a combination of normal slowing metabolic processes in addition to the advanced progression of diabetes within the subject. The rats were subjected to a 2-week acclimatization period necessary to induce Type 2 diabetes through the Purina 5008 food, such that the diet-induced diabetic state was achieved in n=3 rats at the time of the surgical procedure. The control ZDF rat was given a normal rat chow (info on chow). On the day of surgery, the diabetic rats weighed an average of 379±23 g while the control rat weighted 314 g Rats were initially anesthetized in a vented anesthesia chamber using 4-5% isoflurane, and kept at 1-3% for the remainder of the procedure. Their hair was removed from the back using clippers and Veet, and the skin cleaned using iodine and 70% alcohol. Three 6 mm round skin lacerations, including the panniculosus carnosus, were made on each side of the midline using surgical biopsy punches. Silicone splints 10 mm in inner diameter and 15 mm in outer diameter were then adhered using Superglue to surround all 6 wounds. To ensure that splints were secured in place, they were also sutured onto the skin for reinforcement. Round patches 8 mm in diameter with test compounds were placed in the center of the splints to cover the lacerations. Patches of the same size were cut from waterproof transparent dressing to be used as control. The entirety of the shaved skin was then covered using waterproof transparent dressing to maintain sterility of the surgical areas. Finally, adhesive sports tape was wrapped around rats' torso to protect the surgical area. Rats were then placed into clean cages and remained single house for the rest of the study. Sports tape and 3M were removed to evaluate and photograph wounds on days 7 and 14 after surgery. New 3M and sports tape were used to replace dressing. Diabetic ZDF rats remained on the Purina 5008 diet, while control ZDF rats remained on normal rat chow for the rest of the study.

The layers composing each dressing assembly are detailed in FIG. 9. Wound dressings denoted CS1-CS3 contained a collagen base, a silicone layer containing one of three SNAP amounts: 0.2 mg (CS1), 0.8 mg (CS2), and 1.6 mg (CS3), and a polyurethane cover layer. Dressings with CASP labeling contained a collagen base layer, a silicone layer containing 0.8 mg SNAP, a layer of arginine powder, and a polyurethane cover layer. SAP1-3 dressings contained a base layer of silicone with one of three SNAP amounts: 0.2 mg (SAP1), 0.8 mg (SAP2), and 1.6 mg (SAP3), with a layer of arginine powder above, and a polyurethane cover layer. Dressings labeled 3MS1-3MS3 are composed of a base layer of 3M Tegaderm polyurethane, with a layer of silicone on top with one of three SNAP amounts: 0.2 mg (3MS1), 0.8 mg (3MS2), and 1.6 mg (3MS3). CA labeled dressings contained a collagen base layer and with a secondary collagen layer containing a heavy concentration of arginine above, followed by a polyurethane cover layer on top. CAS dressings contained a collagen base layer, followed by a secondary collagen layer containing a heavy concentration of arginine, followed by a silicone layer containing 0.8 mg SNAP, and a polyurethane cover layer. Dressings labeled "C with Cover" were composed of collagen base layers with a polyurethane membrane cover layer on top. "PCS" dressings were composed of cellulose base layers containing 0.8 mg SNAP with special polyurethane membranes on top. "B" dressings were composed of commercial grade hydroxypropyl methylcellulose (HCMP) base layers with a polyurethane top coat. Dressings with the "CSAP" layer were composed of collagen base layers followed by silicone layers containing 0.8 mg SNAP, followed by arginine powder, and finally a polyurethane cover layer on top. Dressing labeled TST4-TST6 are composed of a base layer of polyurethane, with a layer of cellulose layer containing one of three SNAP amounts: 2 mg (TST4), 2.4 mg (TST5), and 3 mg (TST6), followed by a polyurethane cover layer on top.

Results: The wound size was measured and details about inflammation, scar tissue, or pus formation was noted. Each wound size was calculated by $D = D_1 D_2 64 - 16 D_0 22 D1 + D_2 64 - 3 D_0 4$, where $D_1$ and $D_2$ are the longest and shortest diameters of the wound and $$D_0 = \frac{D_1 - D_2}{D_1 + D_2}.$$

The reduction of wound coverage area after treatment with commercial collagen dressings served as the wound size baseline, with a normalized numerical value of 1. Dressings or treatments with faster progression of wound healing than the commercial collagen dressing have normalized wound size numerical values of <1 and dressings or treatments with slower wound healing have normalized wound size values of >1. Compared with the normalized collagen data, the silicone-based SNAP dressing displayed accelerated wound-healing with an average normalized wound size of 0.728 (SD=0.204, SE=0.156) and the silicone-based with SNAP & arginine displayed a normalized wound size of 0.928 (SD=0.346, SE=0.200), indicating an increased rate of healing of diabetic wounds compared to top of the line and more expensive collagen based dressings currently used in the market. Six laceration wounds were created on the back of ZDF rats following IACUC approved protocol on anesthesia, and silicone, bandages, and SNAP & Silicone wound dressing were applied and secured. 7 days of recovery time was given before and bandages were removed around day 5, and photographs and measurements of the wound size were taken again. n=6 measurements of all different wound dressing types in ZDF diabetic rats are shown in FIG. 4. The silicone-based dressings with added SNAP displayed a normalized wound size of 0.799 (SD=0.204, SE=0.083). The p-value for silicone and SNAP based, nitric oxide (NO) releasing, wound-healing dressings over a standard collagen bandage from both studies were applied to n=6 Type 2 diabetic (ZDF) rats treated with silicone based and added SNAP over the standard collagen dressing is 0.037, which is statistically significant.

Figure 10:
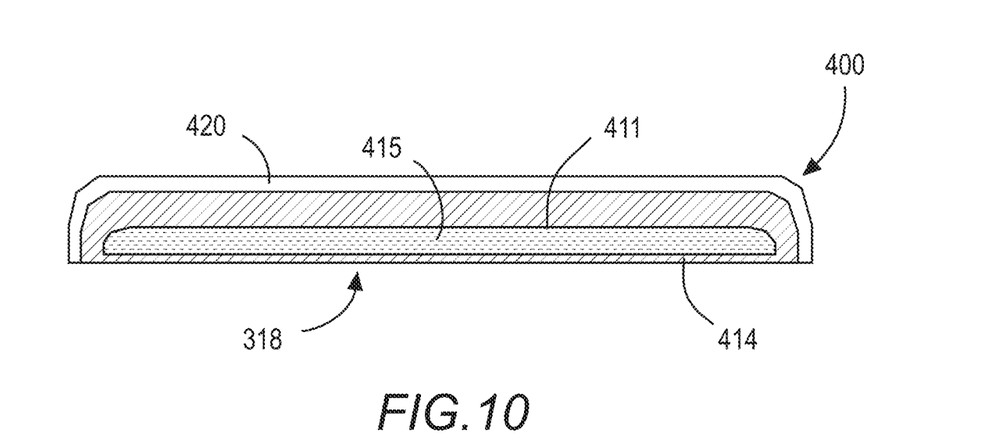
FIG. 10 shows a medical device pad with a first layer and a second layer.

In accordance with yet another embodiment, as illustrated in FIG. 10, a multi-phase pad 400 is provided for treating a wound in accordance with various phases. The multi-phase pad can comprise a first layer, wherein the first layer comprises a transport medium 414 forming a cavity 411, and a nitric oxide donor material 415 disposed within the cavity. The nitric oxide donor material may comprise a powdered material, a mixture, or may be embedded in a holding material as described herein. In addition to the first layer, the multi-phase pad (medical device) comprises a second layer 420, wherein the second layer comprises arginine, EDTA, citrulline, NOSTRIN, arigininosuccinate, L-citrulline malate, tetrahydrobiopterin, ornithine, or a combination thereof. These materials being hosted in the second layer provide the second phase of treatment with benefits to reduce the activity of proteases to promote preferential differentiation of M1 macrophages to M2 macrophages or act as a NO enhancer.

Figure 11:
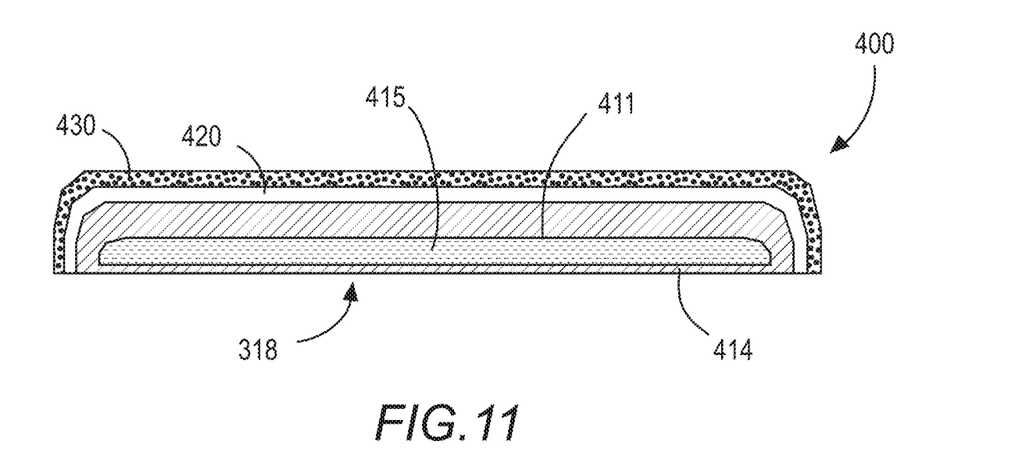
FIG. 11 shows a medical device pad with a first layer, a second layer and a third layer.

Optionally, the multi-phase pad may comprise re-epithelialization benefits to promote cellular proliferation and migration for the formation of granulation tissue. In order to achieve this, the device may include as the second layer (420, FIG. 10) in addition to the nitric oxide donor material layer, or as a third layer (430, FIG. 11) in addition to the NO donor material and the EDTA layer described above, a layer which comprises: cellulose, collagen, citrulline, arginine, tetrahydrobiopterin, ornithine, Nitric Oxide Synthase Trafficking Inducer (NOSTRIN), arigininosuccinate, L-citrulline malate, polyglucose, polyacrylonitrile, polykeratin, siloxane, polyester, polyurethane, polyfibrin, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, or a combination thereof.

Accordingly, a multi-phase pad can comprise a first layer that is configured to deploy nitric oxide in a first phase; a second layer that is configured to deploy EDTA or other activity modulating agent or differentiation agent in a second phase subsequent to the first phase; and optionally a third layer that is configured to deploy collagen or other re-epithelialization agent in a third phase subsequent to the second phase.

Alternatively, a multi-phase pad can comprise a first layer that is configured to deploy nitric oxide in a first phase; a second layer that is configured to deploy collagen or other re-epithelialization agent in a third phase subsequent to the second phase.

Example 4—Medical Tubing

The embodiments described herein, such as a transport medium made of water-permeable materials such as cellulose (cotton, flax, hemp), fabric, polyglucose, polyacrylonitrile, polykeratin, polydimethylsiloxane, polyester, polyurethane, polyfibrin (silk), poly-para-phenylene terephthalamide (Kevlar), and mixtures thereof, that is used in the creation of a biocompatible medical construct may include tubing devices, such as: catheters, implants, feeding tubes, arteriovenous catheters, balloon catheters, sutures, anastomosis rings, resuscitators, drainage tubes, nasal catheters, gastrostomy catheters, and oxygenators. These medical device constructs release NO after catheterization to provide antibacterial, anti-thrombosis, anti-stenosis, and antifungal properties to improve healing and prevent catheter dysfunction.

Example 5—Sock

Figure 12:
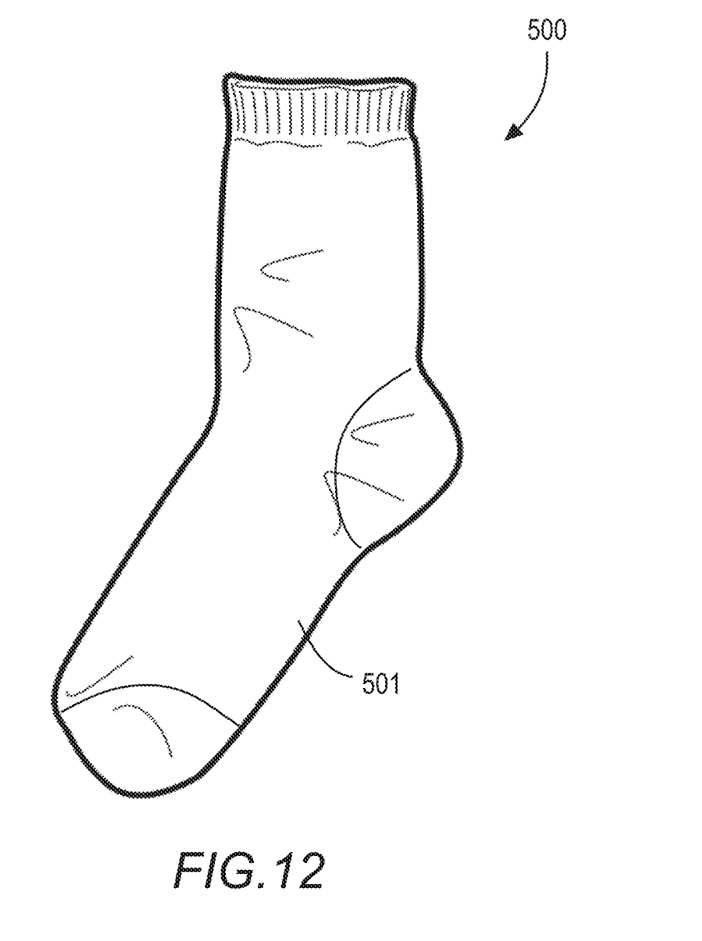
FIG. 12 shows a sock that is knitted with a filament, the filament comprising a transport medium coating the filament and a nitric oxide donor material embedded within the filament.

A filament 501, such as acrylic, cotton, linen, nylon, polyester, polypropylene, rayon, silk, elastane, wool, or other fiber filament, is used to knit a sock 500 for wearing about a foot of a user. Prior to knitting, the filament is saturated in a solution comprising a nitric oxide donor material and a solvent, and subsequently dried by allowing the solvent to evaporate. The resulting filament forms a holding material which holds the nitric oxide donor material therein. The filament is further coated with a polymer or other material as described herein, or otherwise as appreciated by one with skill in the art, that coats the filament to act as a transport medium. The transport medium is permeable by both water and nitric oxide, such that moisture from the user's foot may permeate into the filament of the sock to cause a chemical reaction of the nitric oxide donor material, thereby releasing nitric oxide which ultimately permeates the transport medium and engages the dermal site for anti-microbial therapy.

The sock would be useful as a disposable sock, or one with limited duration, since the nitric oxide would be substantially spent after one wash.

All or a portion of the sock may comprise the filament described above. For example, the filament can be used to knit a ball portion, heel portion, or other portion of a sock, and sewn in with other sock portions to form a completed sock.

Example—Light Modulated NO Release

S-nitroso-N-acetylpenicillamine (SNAP) is mixed with excipients such as cellulose, in a 2.5:1 weight ratio, filled into a silicone urinary Foley catheter center lumen, sealed on both ends with silicone in sections of 2 cm incubated at 37° C. in PBS (pH 7.4, 100 mM EDTA), and NO release measured using a Sievers Nitric Oxide Analyzer (NOA; GE Water and Process Technologies, CO) while purging the solution with N2 (Airgas, Mich.) gas. As an example, while measuring NO release, a UV LED light source (277 nm at 2,500 mW/cm$^2$) was focused at a distance of 2.0 cm from the sample forming a 4 cm$^2$ area of incidence through a square aperture onto the sample, corresponding to an intensity of 2,500 mW/cm$^2$. The light source was also placed at distances of 9.0 cm and 16.0 cm, corresponding to intensities of 625.00 and 277.78 mW/cm$^2$, respectively. The source current to the excitatory LED was controlled by a mechanical switch, and the 360 nm wavelength was chosen since it aligns with peak excitation wavelengths described in various literature sources.

Figure 13:
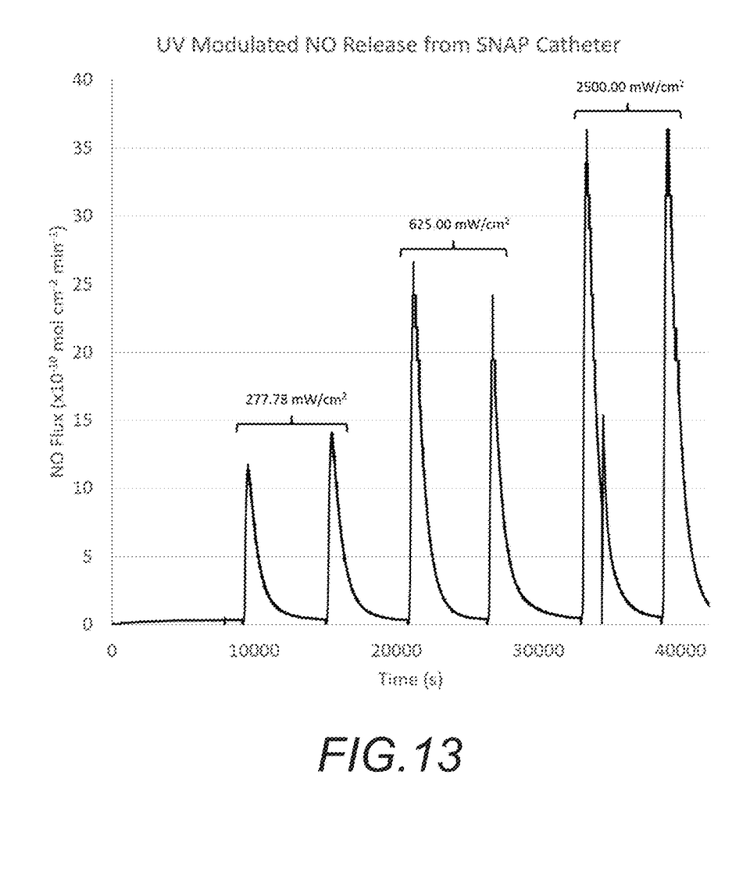
FIG. 13 shows a plot showing UV modulated nitric oxide release from a SNAP catheter.
Figure 14:
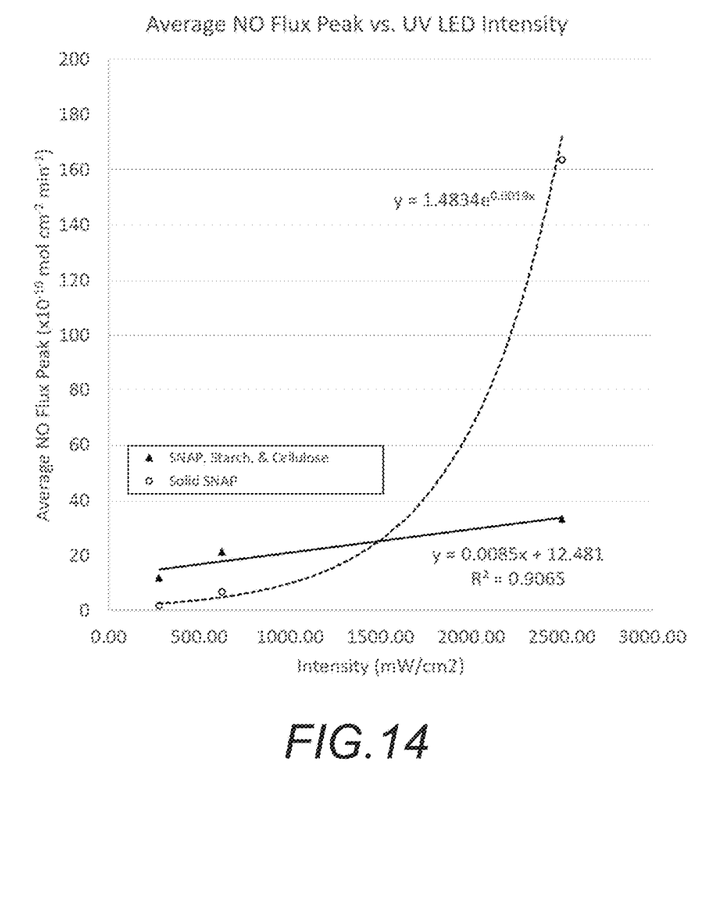
FIG. 14 shows average nitric oxide flux peak vs. UV LED intensity.

FIGS. 13-14 demonstrate NO can be predictably modulated following light activation at 360 nm with 2-minute duration pulses at different irradiance levels 277.78 mW/cm$^2$, 625.00 mW/cm$^2$, and 2,500.00 mW/cm$^2$ at different, and measured NO fluxes were 11.89, 21.31, and 33.23, (all×10$^{-10}$ mol cm$^{-2}$ min$^{-1}$) respectively. Measurements were made at 37° C. using the Sievers Nitric Oxide Analyzer. During the first 30 seconds of the UV LED irradiance, NO release would fall to a minimal baseline, but would surpass the resting NO release plateau of the sample at 37° C. by the end of the 2.0 min pulse. Catheter samples containing only SNAP without excipients were prepared at the same time, and evaluated by the same 260 nm UV modulation protocol to demonstrate that the increased NO release from the sample resulted from the interaction between UV light and SNAP rather than an interaction between UV light and the solid excipients.

CONCLUSION

In accordance with the above details and descriptions, and as supported by the illustrated examples, we hereby disclose:

A medical device, comprising: a transport medium; a cavity being defined and substantially surrounded by the transport medium; the transport medium being permeable to water and nitric oxide; and a nitric oxide donor material disposed within the cavity.

The transport medium may comprise a biocompatible polymer material. The biocompatible polymer material may comprise a water permeability coefficient between 40 and 55000 Barrers. The biocompatible polymer material may further comprise: cellulose, collagen, citrulline, arginine, tetrahydrobiopterin, ornithine, Nitric Oxide Synthase Trafficking Inducer (NOSTRIN), arigininosuccinate, L-citrulline malate, polyglucose, polyacrylonitrile, polykeratin, siloxane, carboxymethyl cellulose, polyester, polyurethane, polyfibrin, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, or a combination thereof.

The nitric oxide donor material may comprise: diazeniumdiolated diamine, S-nitroso-albumin, S-nitroso-N-acetyl-DL-penicillamine (SNAP), S-nitrosoglutathione (GSNO), diazeniumdiolated dibutylhexyldiamine (DBHD N2O2), S-nistrosocystine, Diethylenetriamine/nitric oxide adduct (DETA/NO), Diethylamine NONOate (DEA/NO), Dipropylenetriamine NONOate (DPTA/NO), 6-(2-Hydroxy-1-methyl-2-nitrosohydrazino)-N-methyl-1-hexanamine (MAHMA/NO), 1,2,4-triazole analogues of diclofenac, NCX 4040, ketoprofen-NO hybrids, nitrosoproline (PROLI/NO), spermine (SPER/NO), S-nitroso-N-acetylcysteine, nitroglycerin (GTN), isorbide dinitrate (ISDN) or a combination thereof.

The medical device may further comprise a holding material, wherein the holding material is disposed within the cavity. The holding material may comprise: collagen, cellulose, fabric, polyglucose, polyacrylonitrile, polykeratin, polydimethylsiloxane, polyester, polyurethane, polyfibrin, poly-para-phenylene terephthalamide, polyamide, polysaccharide, poly(lactic-co-glycolic acid), siloxane, nylon, aliphatic, or semi-aromatic polyamides, or a combination thereof. In some embodiments, the nitric oxide donor material can be embedded within the holding material.

The transport medium may comprise a nitric oxide permeability of 0.1 to 8.0 NO Flux Units. For purposes herein, a NO Flux Unit is defined as $4.1\times10^{-10}$ mol cm$^{-2}$ min$^{-1}$.

The medical device may further comprise an excipient, such as a filler material, bulking agent, inert material, or other material that is combined with the nitric oxide donor material for purposes of dispersing the nitric oxide donor material within the cavity or other useful purpose as would be recognized by one with skill in the art. The excipient may comprise a monosaccharide, a disaccharide, a polysaccharide, a polyhydric alcohol, a polypeptide, or a combination thereof. The excipient may comprise: collagen, cellulose, glucose, corn starch, crosspovidone, carboxymethyl cellulose, gelatin, hydroxypropyl cellulose, hydroxypropyl methyl cellulose (HPMC), sorbitol, xylitol, lactose hydrous or anhydrous or monohydrate or spray dried, povidone (PVP), poly(lactic-co-glycolic acid), Talc, silicone, pure acrylic, modified acrylic, natural rubber, synthetic rubber, epoxy, polyurethane, isocyanate, carboxymethyl cellulose, alginate, gelatin, agarose, or a combination thereof.

In some embodiments, the biocompatible polymer material may comprise an α-acetal moiety, a β-acetal moiety, a hydroxyl moiety, a nitrile moiety, a nitrate ester moiety, a pro-alpha2(I) moiety, a carboxyl moiety, or a combination thereof.

While a myriad of possible implementations will be appreciated by one with skill in the art, specific examples may include: a transdermal patch, catheter, implantable device, implantable pouch, implantable patch, anastomosis ring, woven material, diabetic foot ulcer wound dressing, chronic wound dressing, burn wound dressing, trauma wound dressing, mouth ulcer pad, negative pressure wound dressing accessory, wipe, swab stick, gauze accessory, condom, acne pad, acne wipe, facial mask, or a sock.

The transport medium may be configured to communicate light from a light source to the nitric oxide donor material, wherein the light comprises a wavelength between 240 nm and 650 nm.

In another embodiment, the medical device includes a first layer and a second layer, wherein the first layer includes the transport medium, cavity and nitric oxide donor material, and wherein the second layer comprises: arginine, EDTA, citrulline, NOSTRIN, arigininosuccinate, L-citrulline malate, tetrahydrobiopterin, ornithine, or a combination thereof. The medical device may further comprise a third layer, wherein the third layer comprises: cellulose, collagen, citrulline, arginine, tetrahydrobiopterin, ornithine, Nitric Oxide Synthase Trafficking Inducer (NOSTRIN), ariginino-succinate, L-citrulline malate, polyglucose, polyacrylonitrile, polykeratin, siloxane, polyester, polyurethane, polyfibrin, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, or a combination thereof. In this regard, the first layer is configured to deploy nitric oxide in a first phase; the second layer is configured to deploy EDTA in a second phase subsequent to the first phase; and the third layer is configured to deploy collagen in a third phase subsequent to the second phase.

In another aspect, a method for practicing the invention comprises the step of (i) contacting a body of a patient with a medical device as described herein.

In another embodiment, the method comprises: (i) selecting a nitric oxide donor material, (ii) selecting an excipient to modulate nitric oxide release rates from the nitric oxide donor material, (iii) combining the nitric oxide donor material and the excipient to form a mixture, (iv) spreading the mixture within a cavity resident within at least a portion of a device, and (v) sealing the cavity with a material that is semipermeable to both water and nitric oxide.

In yet another embodiment, the method comprises: (i) selecting a nitric oxide donor, (ii) dissolving the nitric oxide donor in a solvent to form a solution, (iii) placing a holding material within the solution to absorb a portion or the entirety of the solution, (iv) evaporating the solution such that at least a portion of the nitric oxide donor is suspended by the holding material, and (v) placing the holding material within the reservoir.

INDUSTRIAL APPLICABILITY

The invention may be practiced in various embodiments to provide a medical device that is configured to provide a nitric oxide rich environment to surrounding tissue for achieving anti-microbial and anti-thrombogenic therapeutic benefits.

Additionally, methods for providing anti-microbial and anti-thrombogenic benefits to a medical patient are disclosed.

As such, the invention is applicable to medical products and procedures.

REFERENCE SIGNS LIST (11) first lumen/lumen cavity
(12) second lumen
(13) third lumen
(14) transport medium
(15) nitric oxide donor material
(16a; 16b) plugs
(17; 317) holding material
(100; 200; 300; 400; 500) medical device
(311; 411) cavity
(315; 415) nitric oxide donor material
(314a; 314b; 414) transport medium
(318) flat contour
(319) coating
(420) second layer
(430) third layer
(501) filament with embedded nitric oxide donor material

What is claimed is:

1. A medical device, comprising:
a transport medium; and
a cavity being contained within the transport medium; and
a woven material disposed within the cavity and surrounded by the transport medium;
characterized in that:
the transport medium is permeable to water and nitric oxide,
the transport medium comprises a water permeability coefficient between 40 and 55000 Barrers, and
the woven material comprises a nitric oxide donor material embedded therein.

2. The medical device of claim 1, wherein the transport medium comprises a biocompatible polymer material.

3. The medical device of claim 2, wherein the biocompatible polymer material comprises: cellulose, collagen, citrulline, arginine, tetrahydrobiopterin, ornithine, Nitric Oxide Synthase Trafficking Inducer (NOSTRIN), ariginino-succinate, L-citrulline malate, polyglucose, polyacrylonitrile, polykeratin, siloxane, carboxymethyl cellulose, polyester, polyurethane, polyfibrin, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, or a combination thereof.

4. The medical device of claim 1, wherein the nitric oxide donor material comprises: diazeniumdiolated diamine, S-nitroso-albumin, S-nitroso-N-acetyl-DL-penicillamine (SNAP), S-nitrosoglutathione (GSNO), diazeniumdiolated dibutylhexyldiamine (DBHD N202), S-nistrosocystine, Diethylenetriamine/nitric oxide adduct (DETA/NO), Diethylamine NONOate (DEA/NO), Dipropylenetriamine NONOate (DPTA/NO), 6-(2-Hydroxy-1-methyl-2-nitrosohydrazino)-N-methyl-1-hexanamine (MAHMA/NO), 1,2,4- triazole analogues of diclofenac, NCX 4040, ketoprofen-NO hybrids, nitrosoproline (PROLI/NO), spermine (SPER/NO), S-nitroso-N-acetylcysteine, nitroglycerin (GTN), isorbide dinitrate (ISDN) or a combination thereof.

5. The medical device of claim 1, wherein the holding woven material comprises: collagen, cellulose, fabric, polyglucose, polyacrylonitrile, polykeratin, polydimethylsiloxane, polyester, polyurethane, polyfibrin, poly-para-phenylene terephthalamide, polyamide, polysaccharide, poly (lactic-co-glycolic acid), siloxane, nylon, aliphatic, or semi-aromatic polyamides, or a combination thereof.

6. The medical device of claim 1, wherein the nitric oxide donor material is embedded within the woven material.

7. The medical device of claim 1, wherein the transport medium comprises a nitric oxide permeability of 0.1 to 8.0 Flux Units.

8. The medical device of claim 1, further comprising an excipient.

9. The medical device of claim 8, wherein the excipient comprises a monosaccharide, a disaccharide, a polysaccharide, a polyhydric alcohol, a polypeptide, or a combination thereof.

10. The method of claim 8, wherein the excipient comprises: collagen, cellulose, glucose, corn starch, crosspovidone, carboxymethyl cellulose, gelatin, hydroxypropyl cellulose, hydroxypropyl methyl cellulose (HPMC), sorbitol, xylitol, lactose hydrous or anhydrous or monohydrate or spray dried, povidone (PVP), poly(lactic-co-glycolic acid), Talc, silicone, pure arcylic, modified arcylic, natural rubber, synthetic rubber, epoxy, polyurethane, isocyanate, carboxymethyl cellulose, alginate, gelatin, agarose, or a combination thereof.

11. The medical device of claim 2, wherein the biocompatible polymer material comprises an α-acetal moiety, a β-acetal moiety, a hydroxyl moiety, a nitrile moiety, a nitrate ester moiety, a pro-alpha2(I) moiety, a carboxyl moiety, or a combination thereof.

12. The medical device of claim 1, wherein the medical device comprises: a transdermal patch, catheter, implantable device, implantable pouch, implantable patch, anastomosis ring, woven material, diabetic foot ulcer wound dressing, chronic wound dressing, burn wound dressing, trauma wound dressing, mouth ulcer pad, negative pressure wound dressing accessory, wipe, swab stick, gauze accessory, condom, acne pad, acne wipe, facial mask, or a sock.

13. The medical device of claim 1, wherein the transport medium is configured to communicate light from a light source to the nitric oxide donor material, wherein the light comprises a wavelength between 240 nm and 650 nm.

14. The medical device of claim 1, said device comprising a first layer and a second layer, wherein the first layer includes the transport medium, cavity and nitric oxide donor material, and wherein the second layer comprises: arginine, EDTA, citrulline, NOSTRIN, arigininosuccinate, L-citrulline malate, tetrahydrobiopterin, ornithine, or a combination thereof.

15. The medical device of claim 14, further comprising a third layer, wherein the third layer comprises: cellulose, collagen, citrulline, arginine, tetrahydrobiopterin, ornithine, Nitric Oxide Synthase Trafficking Inducer (NOSTRIN), arigininosuccinate, L-citrulline malate, polyglucose, polyacrylonitrile, polykeratin, siloxane, polyester, polyurethane, polyfibrin, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, or a combination thereof.

16. The medical device of claim 15, wherein the first layer is configured to deploy nitric oxide in a first phase; the second layer is configured to deploy EDTA in a second phase subsequent to the first phase; and the third layer is configured to deploy collagen in a third phase subsequent to the second phase.

17. A method, comprising:
contacting a body of a patient with the medical device of claim 1.

18. A medical device, comprising:
a transport medium;
a cavity being defined and substantially surrounded by the transport medium;
the transport medium being permeable to water and nitric oxide; and
a nitric oxide donor material disposed within the cavity, characterized in that:
the nitric oxide donor material is embedded within a woven material.

* * * * *